(12) United States Patent
Zhang et al.

(10) Patent No.: US 10,849,997 B2
(45) Date of Patent: Dec. 1, 2020

(54) DISINFECTION DEVICE HAVING DISINFECTION LIGHT SOURCE

(71) Applicant: Bolb Inc., Livermore, CA (US)

(72) Inventors: Jianping Zhang, Arcadia, CA (US); Ling Zhou, Dublin, CA (US); Ying Gao, Fremont, CA (US)

(73) Assignee: BOLB INC., Livermore, CA (US)

( * ) Notice: Subject to any disclaimer, the term of this patent is extended or adjusted under 35 U.S.C. 154(b) by 0 days.

(21) Appl. No.: 16/155,888

(22) Filed: Oct. 10, 2018

(65) Prior Publication Data

US 2020/0114027 A1 Apr. 16, 2020

(51) Int. Cl.
*A61L 2/10* (2006.01)
*A61L 2/26* (2006.01)

(52) U.S. Cl.
CPC ...... *A61L 2/10* (2013.01); *A61L 2/26* (2013.01); *A61L 2202/11* (2013.01); *A61L 2202/121* (2013.01); *A61L 2202/122* (2013.01)

(58) Field of Classification Search
CPC ............. A61L 2202/14; A61L 2202/11; A61L 2202/16; A61L 2202/23; A61L 2/08; A61L 2/24; A61L 2202/24; A61L 2202/25; A61L 2209/212; A61L 2/0011; A61L 2/26; A61L 2/28; A61L 9/20; C02F 1/325; C02F 2201/326; C02F 2201/009; C02F 2201/3228; C02F 1/32; C02F 2303/04
USPC ....... 250/455.11, 432 R, 228, 372, 373, 435, 250/453.11, 504 R; 210/143, 192, 739, 210/748.03, 748.04, 748.1; 422/22, 1
See application file for complete search history.

(56) References Cited

U.S. PATENT DOCUMENTS

| | | | | |
|---|---|---|---|---|
| 4,806,770 A | * | 2/1989 | Hylton | A47K 1/09 250/455.11 |
| 6,766,097 B2 | * | 7/2004 | Horton, III | A61L 2/10 210/636 |
| 8,426,800 B2 | * | 4/2013 | Ingram | G02B 5/02 250/228 |
| 8,475,714 B2 | * | 7/2013 | Barak | C02F 1/32 119/200 |
| 8,816,300 B1 | * | 8/2014 | Walker | C02F 1/325 250/453.11 |
| 8,975,596 B1 | * | 3/2015 | Matthews | C02F 1/325 250/432 R |
| 9,346,687 B1 | * | 5/2016 | Matthews | C02F 1/325 |
| 9,364,573 B2 | * | 6/2016 | Deshays | A61L 2/24 |
| 9,387,268 B2 | * | 7/2016 | Farren | A61L 2/10 |
| 9,468,695 B2 | * | 10/2016 | Liao | A61L 2/10 |
| 9,707,306 B2 | * | 7/2017 | Farren | A61L 2/10 |
| 10,195,299 B2 | * | 2/2019 | Baker | A61L 2/10 |
| 2003/0030011 A1 | * | 2/2003 | Brown | A61L 2/0011 250/455.11 |
| 2012/0006995 A1 | * | 1/2012 | Greuel | C02F 1/325 250/373 |

(Continued)

*Primary Examiner* — David A Vanore
(74) *Attorney, Agent, or Firm* — Patent Office of Dr. Chung Park

(57) ABSTRACT

A disinfection device includes: a container having a wall that defines a chamber for containing liquid therein; and a light source for transmitting disinfection light to the liquid. The light source is in a spatial relationship with the container so that a distance between the light source and the first light receiving surface of the liquid remains unchanged regardless of a volume of the liquid.

9 Claims, 9 Drawing Sheets

(56) References Cited

U.S. PATENT DOCUMENTS

2014/0110351 A1\* 4/2014 Fahs, II ................... C02F 1/32
210/748.11

\* cited by examiner

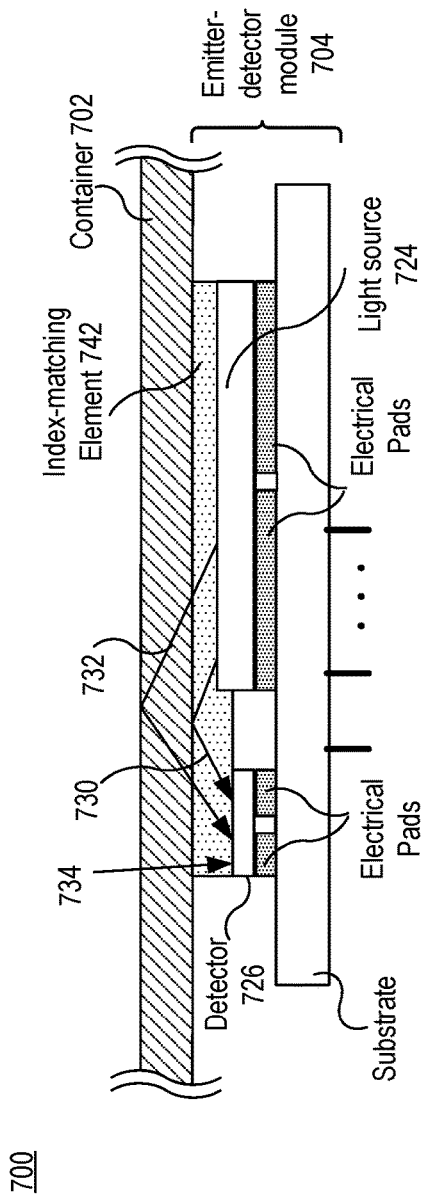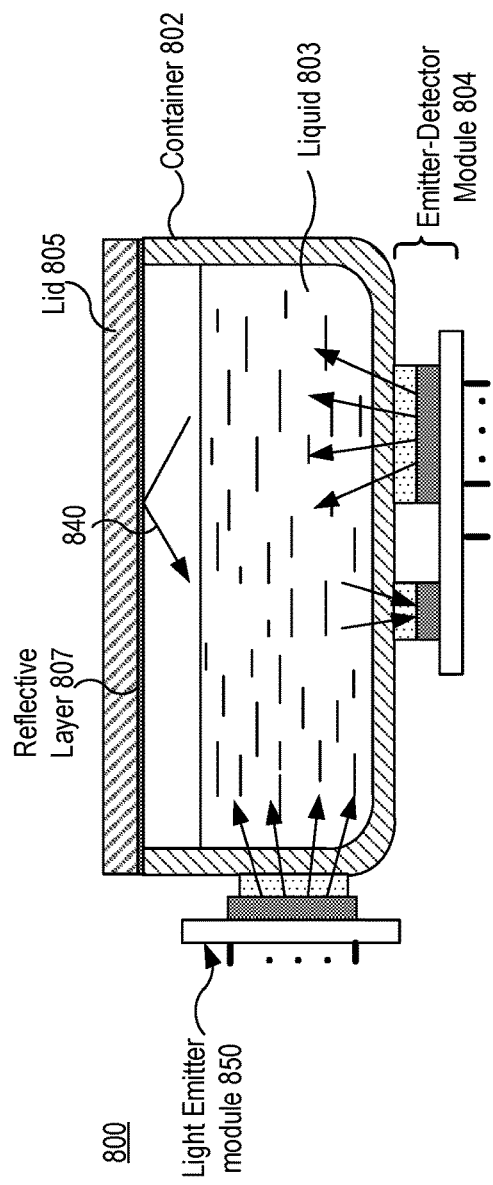

DISINFECTION DEVICE HAVING DISINFECTION LIGHT SOURCE

BACKGROUND

A. Technical Field

The present invention relates to disinfection devices, and more particularly, to devices that have disinfection light sources.

B. Background of the Invention

Disinfection light sources have become widely used to disinfect various types of tools and accessories, such as contact lens, scissors, tweezers, nail drill bits, and so on. Typically, the tools and accessories are submerged in the disinfection fluid filled in a container and exposed to ultraviolet (UV) light for disinfection. FIG. 1 shows a conventional disinfection device 100 having a disinfection light source 106. As depicted, a volume of liquid 103 is filled in the container 102, where one or more objects (not shown in FIG. 1) are submerged in the liquid 103. The light source 106, which is mounted on a circuit board 104, emits disinfection light 108 toward the container 102 to thereby disinfect the objects in the liquid 103.

FIG. 2 is an enlarged view of the inset diagram 120 in FIG. 1. As depicted, a portion 136-1 of the disinfection light 134 is reflected at the interface between the air 122 and liquid 103 and the rest 136-2 is refracted into the liquid 103. If the disinfection light 134 is s-polarized, the reflectance, Rs, at the interface is given as Equation (1):

$$R_s = \left|\frac{n_1\cos\vartheta_i - n_2\cos\theta_t}{n_1\cos\vartheta_i + n_2\cos\theta_t}\right|^2 \quad (1)$$

where, $n_1$, $n_2$, $\Theta_i$, and $\Theta_t$ represent the index of refraction of first medium (e.g. air 122), index of refraction of the second medium (e.g. liquid 103), incidence angle, and refraction angle, respectively. Similarly, if the disinfection light 134 is p-polarized, the reflectance, Rp, at the interface is given as Equation (2):

$$R_p = \left|\frac{n_1\cos\vartheta_t - n_2\cos\theta_i}{n_1\cos\vartheta_t + n_2\cos\theta_i}\right|^2 \quad (2)$$

By way of example, assuming that the incidence angle of the light 132 is 0 degree and the index of refraction $n_2$ of the liquid is 1.33, the reflectance at the interface between the air and liquid is 0.02 and the transmittance at the interface is 0.98. In general, the reflectance of the s- and p-polarized lights at an interface increases as the difference in the indices of refraction (or, equivalently, refractive indices) between the two media increases.

FIG. 3 shows a conventional disinfection device 300. As depicted, the disinfection device 300 is similar to the disinfection device 100, with the difference that the disinfection device 300 includes a lid 305 that covers the top of the container 302. Typically, the lid 305 is formed of material that is transparent to the disinfection light 308 generated by the light source 306. FIG. 4 is an enlarged view of the inset diagram 320 in FIG. 3. As depicted, the disinfection light 308 is reflected at the three interfaces: the first interface between the air 322 and the lid 305; the second interface between the lid 305 and air 324; and the third interface between the air 324 and the liquid 303. As indicated by the arrows 334, 336 and 338, portions of the disinfection light 332 are reflected at the three interfaces, where the incidence angle is 0 degree. Similarly, the arrows 340, 342, and 344 show portions of the disinfection light that are reflected at the three interfaces. For simplicity, the portions of the disinfection light refracted at the three interfaces are not shown in FIG. 4.

In general, the total transmittance of the disinfection light 308, which represents a fraction of the disinfection light 308 that enters the liquid 303, decreases as the number of interfaces increases along the passageway of light from the light source 306 to the liquid 303 and also as the difference in refractive indices between the two media at each interface increases.

As described in conjunction with FIGS. 1-4, the conventional disinfection devices include light loss mechanisms that reduce the total transmittance of light from the light source to the liquid. In general, the overall operational efficiency of a disinfection device decreases as the transmittance decreases. As such, there is a need for a disinfection device having enhanced transmittance of the disinfection light from the light source to the container.

Another problem of the conventional disinfection devices is that the light intensity on the top surface of the liquid changes as the distance from the light source 106 to the liquid surface changes. As shown in FIG. 1, the distance D between the light source 106 and the top surface of the liquid 103 increases as the liquid 103 evaporates, for instance. Since the intensity of the disinfection light 108 at the top surface of the liquid 103 is inversely proportion to the distance D, the intensity of the disinfection light entering the liquid 103 decreases as the distance D increases. Also, the disinfection light 108 is absorbed by the air filling the gap between the light source 106 and the top surface of the liquid 103, further decreasing the intensity of disinfection light entering the liquid 103. As the intensity of the light entering the liquid 103 changes, the amount of light entering the liquid also changes.

The distance D may change due to other factors. For instance, the user may fill the container 102 with different amount of liquid 103 for different disinfection cycles. Since the intensity of disinfection light 108 changes as the distance D changes, the variation of the distance D may affect the performance of the disinfection device 100. To ensure safe level of sterilization of the bacteria/germs in the liquid 103 and any object submerged in the liquid, the amount of the light entering the liquid 103 needs to be higher than a minimum threshold. Thus, if the distance D changes, the device 100 may require a mechanism to compensate the variation of the distance D, which increases the complexity and manufacturing cost of the device 100. As such, there is a need for a disinfection device that maintains a fixed intensity of light at the liquid surface through which the light enters the liquid regardless of the volume of the liquid.

SUMMARY OF THE DISCLOSURE

In one aspect of the present invention, a disinfection device includes: a container having a wall that defines a chamber for containing liquid therein; and a light source for transmitting disinfection light to the liquid; wherein the light source is in a spaced-apart relationship with the container so that a distance between the light source and a first light receiving surface of the liquid remains unchanged regardless of the volume of the liquid.

In another aspect of the present invention, a disinfection device includes: a container having a wall that defines a chamber and is formed of a material having a first refractive index; a light source having a top portion and transmitting disinfection light to the wall of the container through the top portion, the top portion being formed of material having a second refractive index; a first index-matching element directly contacting both the wall of the container and the top portion of the light source, the first index-matching element being formed of material having a third refractive index; and the third refractive index being equal to or greater than a smaller one of the first and second refractive indices, the third refractive index being equal to or less than a greater one of the first and second refractive indices.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 7 is a cross sectional view of a disinfection device according to embodiments of the present disclosure.

FIG. 8 is a cross sectional view of a disinfection device according to embodiments of the present disclosure.

DETAILED DESCRIPTION OF THE PREFERRED EMBODIMENTS

In the following description, for the purposes of explanation, specific details are set forth in order to provide an understanding of the disclosure. It will be apparent, however, to one skilled in the art that the disclosure can be practiced without these details. One skilled in the art will recognize that embodiments of the present disclosure, described below, may be performed in a variety of ways and using a variety of means. Those skilled in the art will also recognize additional modifications, applications, and embodiments are within the scope thereof, as are additional fields in which the disclosure may provide utility. Accordingly, the embodiments described below are illustrative of specific embodiments of the disclosure and are meant to avoid obscuring the disclosure.

A reference in the specification to "one embodiment" or "an embodiment" means that a particular feature, structure, characteristic, or function described in connection with the embodiment is included in at least one embodiment of the disclosure. The appearance of the phrase "in one embodiment," "in an embodiment," or the like in various places in the specification are not necessarily all referring to the same embodiment.

Figure 5:
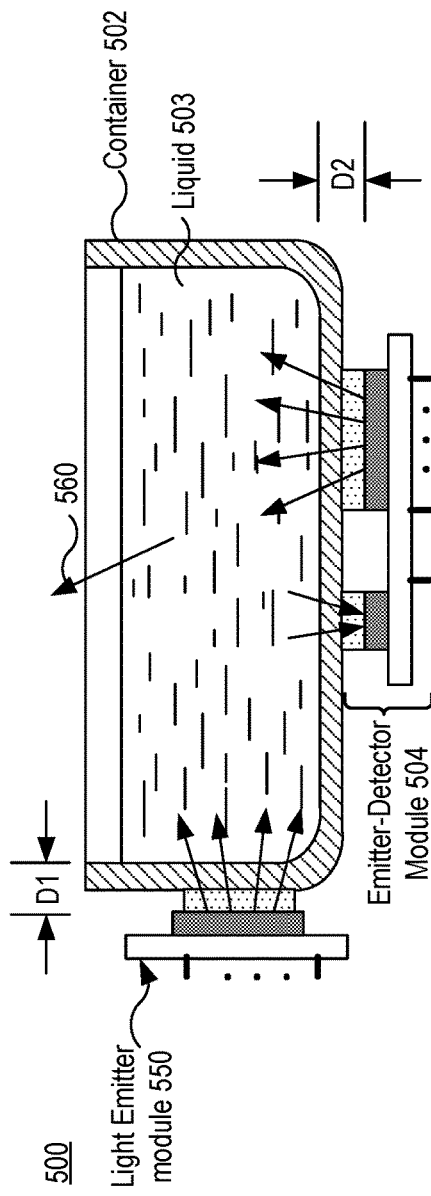
FIG. 5 is a cross sectional view of a disinfection device according to embodiments of the present disclosure.

FIG. 5 is a cross sectional view of a disinfection device 500 according to embodiments of the present disclosure. As depicted, the disinfection device 500 may include: a container 502 for holding a volume of liquid 503 therein; and an emitter-detector module 504 for generating disinfection light and detecting a portion of the disinfection light. Optionally, the disinfection device 500 may include a light emitter module 550 for generating disinfection light. It is noted that the disinfection device 500 may include any suitable number of emitter-detector modules and/or light emitter modules.

Figure 1:
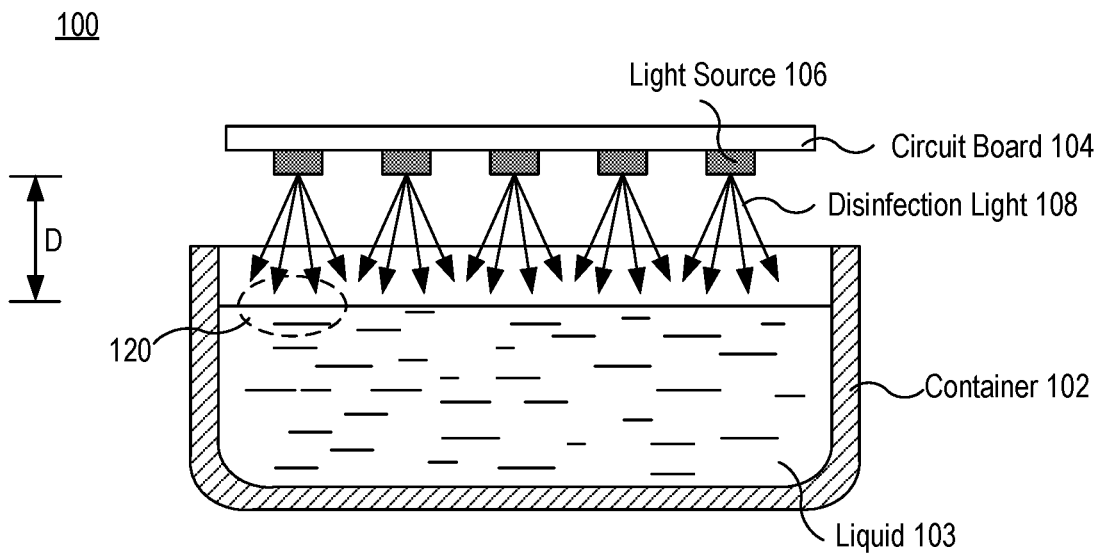
FIG. 1 shows a conventional disinfection device.
Figure 2:
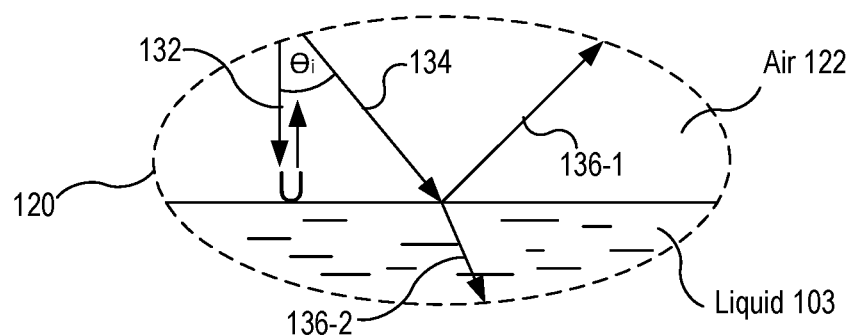
FIG. 2 shows an enlarged view of an inset diagram in FIG. 1.
Figure 3:
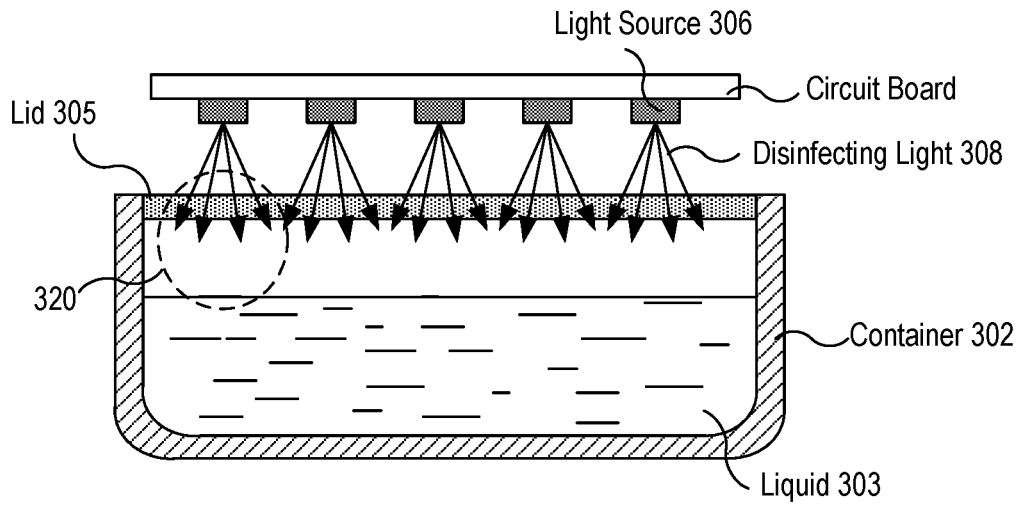
FIG. 3 shows a conventional disinfection device.
Figure 4:
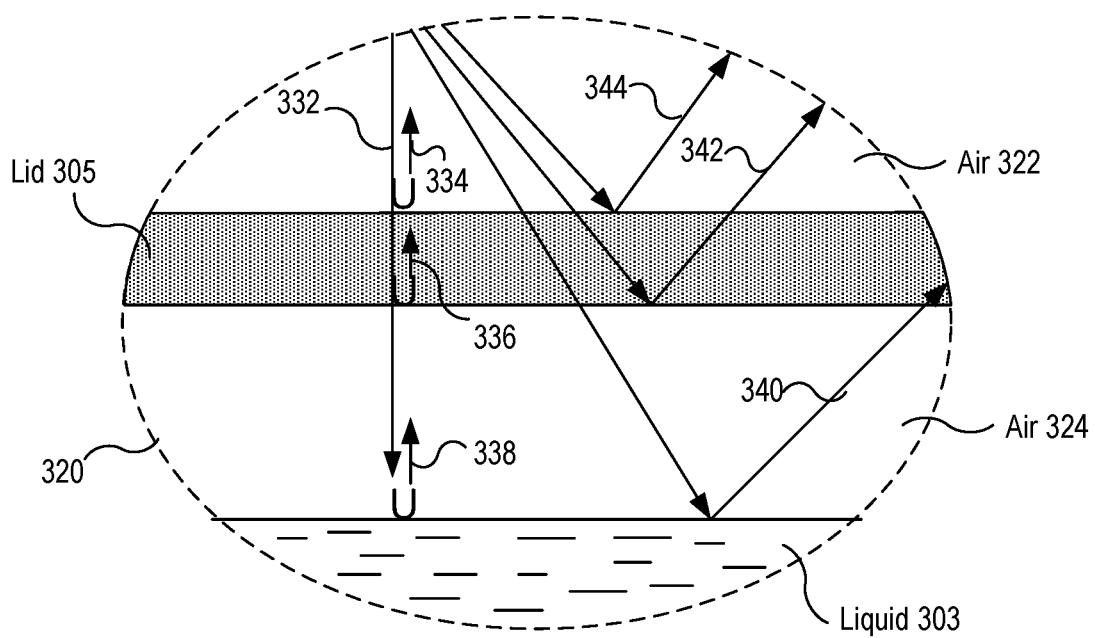
FIG. 4 shows an enlarged view of an inset diagram in FIG. 3.

In embodiments, the emitter-detector module 504 (or light emitter module 550) may be in a spatial relationship with the container 502 so that the distance between the light source in the emitter-detector module (or the light emitter) and the first light receiving surface of the liquid remains unchanged regardless of the volume of the liquid. (Hereinafter, the first light receiving surface refers the surface of liquid through which the disinfection light enters the liquid for the first time after leaving the light source.) As discussed in conjunction with FIG. 1, in the conventional systems, the distance D between the light source and the top surface of the liquid may change, resulting in the variation of the light intensity and amount entering the liquid. In contrast, the light emitter module 550 may be located on the side wall of the container 502 so that the distance D1 between the light source and the light receiving surface of the liquid 502 remains unchanged, even if the top surface the liquid 503 (i.e., the volume of the liquid) changes. Similarly, the distance D2 between the light source 524 in the emitter-detector module 504 and the light receiving surface of the liquid 503 remain unchanged, even if the top surface the liquid 503 (i.e., the volume of the liquid) may change. Since the distance D1 (and D2) remains fixed regardless of the volume of the liquid, the same amount of disinfection light may be delivered to the liquid 503 during each disinfection cycle, enhancing the repeatability of the disinfection process.

The container 502 may be formed of material that is transparent to the disinfection light generated by the emitter-detector module 504 and light emitter module 550. The liquid 503 may be any suitable disinfection fluid, such as contact lens cleaning fluid. In embodiments, one or more tools and accessories may be submerged in the liquid 503 and sterilized/disinfected by the disinfection light. In embodiments, the disinfection light may be UV light or any other light suitable for germicidal and medical applications.

Figure 6:
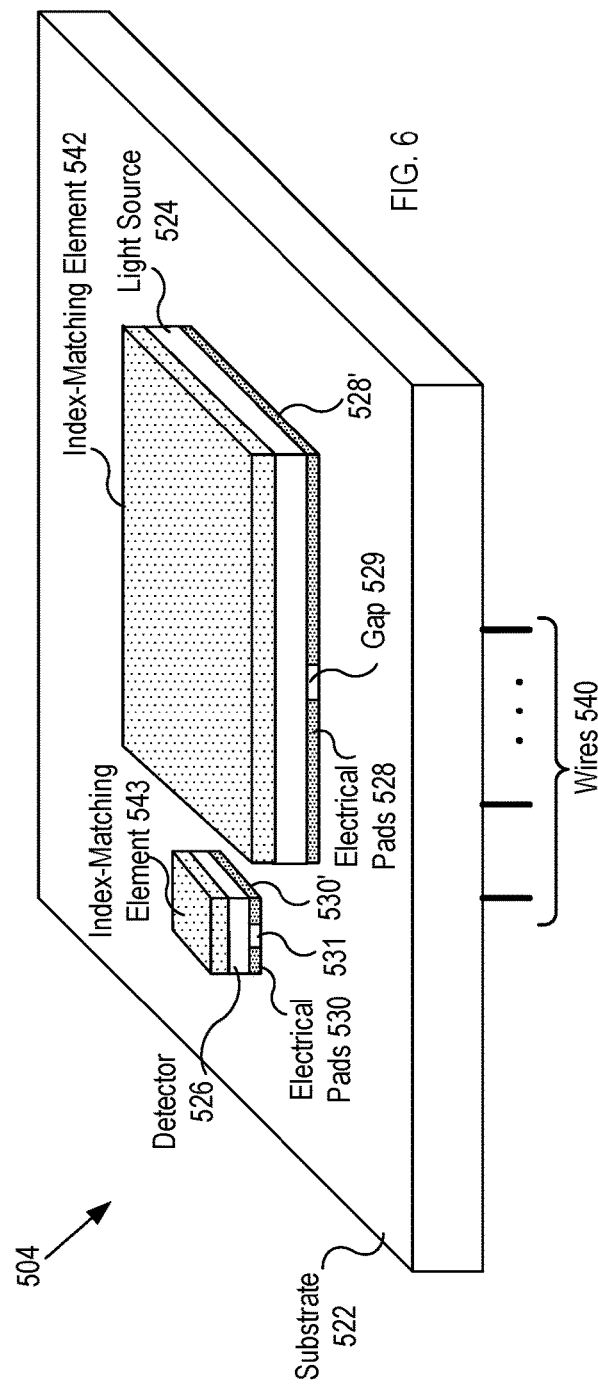
FIG. 6 shows a perspective view of the emitter-detector module of the disinfection device in FIG. 5.

FIG. 6 shows a perspective view of the emitter-detector module 504 of the disinfection device 500 in FIG. 5. As depicted, the emitter-detector module 504 may include: a substrate 522 for physically supporting and wiring electrical components mounted thereon; a disinfection light source (or shortly light source) 524 secured to the substrate 522 by electrical pads 528 and 528'; and a light detector (or, shortly detector) 526 secured to the substrate 522 by electrical pads 530 and 530'.

In embodiments, the substrate 522 may be a printed circuit board (PCB) and include conductive tracks, pads, or other features etched from copper sheets laminated onto an electrically non-conductive substrate, such as glass epoxy. The substrate 522 may be single sided (one copper layer), double sided (two copper layers) or multi-layer (such as bottom, middle, top layers) and conductors on different layers may be connected with vias. It is noted that other suitable material, such as ceramic, may be used for the substrate 522.

In embodiments, the light source 524 may be a light emitting diode (LED) that includes layers stacked on a substrate. For instance, the stacked layers may include a buffer layer formed on a sapphire substrate, an n-contact layer coupled to an n-pad/electrode, an n-clad layer, an active layer, a p-clad layer, and a p-contact layer coupled to a p-pad/electrode, and generate the disinfection light, such as UV light, when electrical current is applied through the n-pad and p-pad. In embodiments, the light source 524 may be an AlGaN multiple-quantum-well (MQW) LED with emission wavelengths in the range of 205-365 nm, optionally in the range of 240-280 nm for solar blind applications. In embodiments, the input power to the light source 524 may be controlled so that the intensity of the light from the light source is maintained at the target level to ensure sterilization of the germs in the liquid 503.

In embodiments, the two electrical pads 528 and 528' may be formed of electrically conducting material, such as Au or AuSn, and electrically coupled to the p-pad/electrode and n-pad/electrode of the light source 524, respectively. In embodiments, to secure the light source 524 to the substrate 522, the electrical pads 528 and 528' may be formed on the top surface of the substrate 522 and then the light source 524 may be positioned on the electrical pads 528 and 528'. Subsequently, the electrical pads 528 and 528' may be heated and cured so that the electrical pads 528 and 528' can securely bond the light source 524 to the substrate 522.

The substrate 522 may communicate electrical signals, including the input current (or input power) to the light source, with the light source 524 via the electrical pads 528 and 528'. The gap 529 may electrically separate the electrical pads 528 and 528' from each other and, optionally, may be filled with electrically insulating material.

In embodiments, the detector 526 may be a photodiode that generates electrical signal, photocurrent, in response to a portion of the light that is generated by the light source 524 and reflected by the container 502 and/or liquid 503. In embodiments, the detector 526 may have a light absorbing intrinsic semiconductor layer sandwiched by an n-type and a p-type semiconductor layers forming a so called PIN structure and include a pair of anode and cathode. For instance, the detector 526 may have layers stacked on a sapphire substrate, where the stacked layers may include an n-type epitaxial layer coupled to a first electrode, an active layer (intrinsic layer) for converting UV light into photocurrent, and a p-type epitaxial layer coupled to a second electrode, where the photocurrent flows in the detector 526 from the first electrode to the second electrode. In embodiments, the detector 526 may be an AlGaN PIN photodetector detecting UV light, optionally in the solar blind UV range of 240-280 nm.

In embodiments, the two electrical pads 530 and 530' may be formed of electrically conducting material, such as Au or AuSn, and electrically coupled to the first and second electrodes of the detector 526, respectively. The detector 526 may be mounted on the substrate 522 in the similar manner as the light source 524. In embodiments, the electrical pads 530 and 530' may be formed on the top surface of the substrate 522 and then the detector 526 may be positioned on the electrical pads 530 and 530'. Subsequently, the electrical pads 530 and 530' may be heated and cured so that the electrical pads 530 and 530' can securely bond the detector 526 to the substrate 522.

The substrate 522 may communicate electrical signals, including the output photocurrent from the detector 526, with the detector 526 via the electrical pads 530 and 530'. The gap 531 may electrically separate the electrical pads 530 and 530' from each other and, optionally, may be filled with electrically insulating material. In embodiments, the substrate 522 may send/receive electrical signals to an external device(s) via suitable communication channels, such as the wires 540.

In embodiments, an index-matching layer/element 542 may be disposed between the light source 524 and the container 502, where the index-matching element 542 may be formed of material that is transparent to the disinfection light. In embodiments, the index-matching element 542 may be in direct contact with the light source 524 and container 502, to thereby remove the air gap between the light source 524 and the container 502.

In embodiments, the index of refraction, $n_i$, of index-matching element 542 may be selected so that the transmittance of the disinfection light from the lights source 524 to the container 502 is increased. For instance, the top surface of the light source 524 may be formed of material that has an index of refraction, $n_s$, and the container 502 may be formed of material that has an index of refraction, $n_c$. The disinfection light from the light source 524 passes through the first interface between the top surface of the light source 524 and the index-matching element 542 and the second interface between the index-matching element 542 and the container 502. Thus, the reflections at these two interfaces may be reduced by adjusting the refractive index of the index-matching element 542. In embodiments, the refractive index of the index-matching element 542 may satisfy the following equation:

$$n_s \leq n_i \leq n_c \quad (3)$$

Similarly, if $n_s$ is greater than $n_c$, the index of refraction for the index-matching element 542 may be selected to satisfy the following equation:

$$n_c \leq n_i \leq n_s \quad (4)$$

By way of example, the top surface of the light source 524 may include sapphire coating (n=1.76) and the container 502 may be formed of quarts (1.46). If the device 500 does not include the index-matching element 542 so that there is an air gap between the light source 524 and the container 502, the disinfection light from the light source passes through two interfaces: the first interface between the light source 524 and the air; and the second interface between the air and the container 502. For simplicity, the incidence angle is assumed to be 0 degree. In such a case, the transmittance of the disinfection light from the light source to the container wall is 0.855, according to Equations (3) and (4). In contrast, in embodiments, the index-matching element 542 may be disposed between the light source 524 and the container 502 and directly contact the light source 524 and container 502. By way of example, if the refractive index of the index-matching element 542 is 1.6 and the incidence angle is 0 degree, the transmittance of the disinfection light from the light source 524 to the container 502 is 0.996. Thus, the index-matching element 542 significantly increases the transmittance of the disinfection light, i.e., the reflectance at the interfaces is significantly reduced, compared to the case where the index-matching element 542 is not included in the device 500.

In embodiments, an index-matching element 543 may be disposed between the detector 526 and the container 502, removing the air gap between the detector 526 and the container 502. Based on the same reasons set forth above, the transmittance of the light from the container 502 to the detector 526 is increased by the index-matching element 543, where the index of refraction, $n_i$, of the index-matching element 543 may satisfy the following Equation (5):

$$n_d \leq n_i \leq n_c \quad (5)$$

where $n_d$ represents the refractive index of the material that forms the top (light receiving side) surface of the detector 546. If $n_d$ is greater than $n_c$, the refractive index of the index-matching element 543 may be selected to satisfy the following equation:

$$n_c \leq n_i \leq n_d \quad (6)$$

In embodiments, the index-matching element 542 may be formed of adhesive material that satisfies Equation (3) or (4) so that the light source 524 is secured to the container 502 by the index-matching element 542. Similarly, the index-matching element 543 may be formed of adhesive material that satisfies Equation (5) or (6) so that the detector 546 is secured to the container 502 by the index-matching element 543. In embodiments, the index-matching elements 542 and 543 may be formed of the same material.

As discussed above, the light emitter module 550 may be attached to the container 502. In embodiments, the light emitter module 550 may be similar to the emitter-detector module 504, with the difference that the light emitter module 550 does not include the detector 526, index-matching element 543 and electrical pads 530 and 530'.

FIG. 7 shows a disinfection device 700 according to embodiments of the present disclosure. As depicted, the disinfection device 700 is similar to the disinfection device 500, with the difference that an index-matching element 742 extends from the light source 724 to the detector 726. The material and function of each component of the disinfection device 700 may be similar to those of its counterpart component of the disinfection device 500. In embodiments, the index-matching element 742 may be used to secure the emitter-detector module 704 to the container 702.

In embodiments, a portion of the light from the light source 724 may be transmitted to the detector 726 via various passageways. For instance, a portion of the light from the light source 724 may be internally reflected on the inner surface of the container 702, as indicated by an arrow 732. In another example, as indicated by an arrow 734, a portion of the light that is transmitted through the container 702 may be sent to the detector by various mechanisms, such as scattering by the liquid and multiple reflection within the inner surface of the container 702. In yet another example, a portion of the light from the light source 724 may be internally reflected on the interface between the index-matching element 742 and the outer surface of the container 702 and transmitted through the index-matching element 724 to the detector 726, as indicated by the arrow 730. As such, the index-matching element 742 may not only bond the container 702 to the emitter-detector module 704 but also provide an additional waveguide for transmitting a portion of the light from the light source 724 to the detector 726 therethrough.

Referring back to FIG. 5, a portion of the disinfection light in the liquid 503 may proceed upwardly to escape the container 502, as indicated by an arrow 560. In embodiments, to prevent the light 560 from escaping the container, a lid/cover may be disposed on the container. FIG. 8 is a cross sectional view of a disinfection device 800 according to embodiments of the present disclosure. As depicted, the disinfection device 800 is similar to the disinfection device 500, with the difference that a lid 805 covers the top of the container 802. In embodiments, a reflective layer 807, which may be disposed on the bottom surface of the lid 805, may redirect the disinfection light toward the liquid 803, as indicated by an arrow 840. In embodiments, the reflective layer 807 may be formed of light reflecting material, such as aluminum, silver or distributed Bragg reflector (DBR), deposited on the bottom surface of the lid 805.

Figure 9:
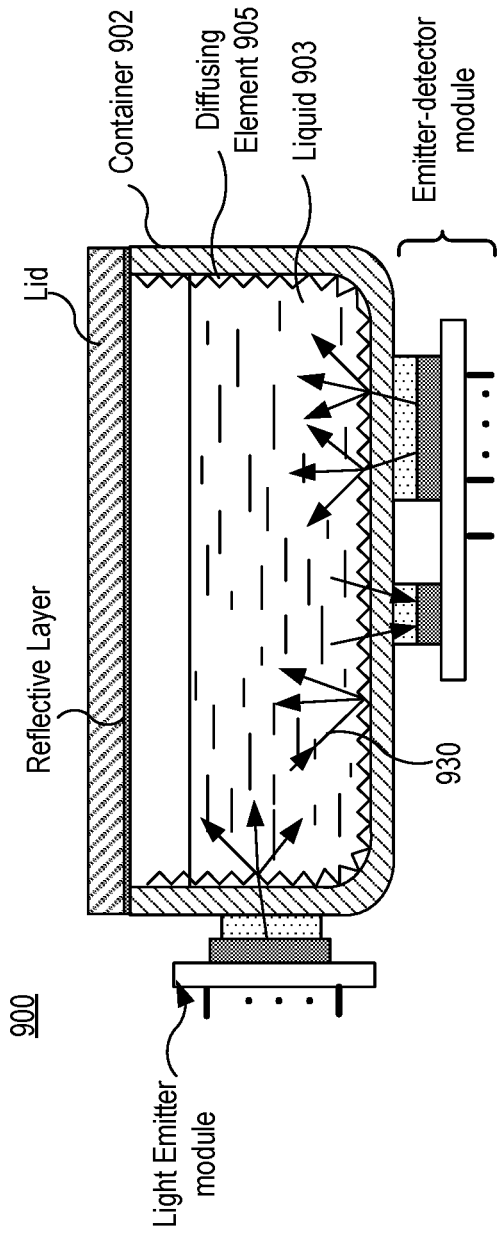
FIG. 9 is a cross sectional view of a disinfection device according to embodiments of the present disclosure.

Some of the tools, such as contact lens, submerged in the liquid 803 and disinfected by the disinfection light may degrade from direct exposure to the disinfection light over an extended period of time. To prevent the tools from being directly exposed to the disinfection light, a diffusing element may be used in the disinfection device. FIG. 9 is a cross sectional view of a disinfection device 900 according to embodiments of the present disclosure. As depicted, the disinfection device 900 is similar to the disinfection device 800, with the difference that a light diffusing element 905 is disposed on the inner surface of the container 902.

In embodiments, the diffusing element 905 may be generated by making a suitable pattern, such as triangular grooves, arrays of dimples or other geometric or random scattering elements, on the inner surface of the container 902 so that the diffused disinfection light is uniformly distributed over the entire liquid 903 in the container 902. In embodiments, the diffusing element 905 may include a patterned layer (or, equivalently, diffuser) that is secured to the inner surface of the container 902 and formed of material that is transparent to the disinfection light.

It is noted that the diffusing element 905 may also prevent the light from escaping from the container 902. As indicated by the arrow 930, the light incident on the diffusing element 905 may be diffused and reflected toward the liquid 903. If the disinfection device 900 does not have the diffusing element 905, the light indicated by the arrow 930 would pass through the container 902. As such, the diffusing element 905 may reduce the leakage of the disinfection light through the container 902.

Figure 10:
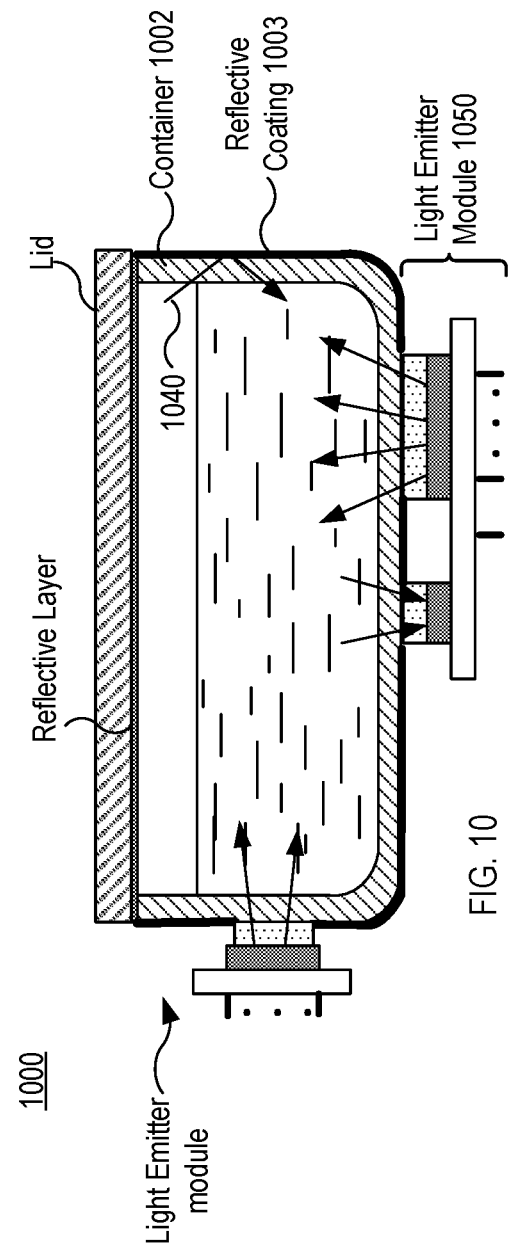
FIG. 10 is a cross sectional view of a disinfection device according to embodiments of the present disclosure.

FIG. 10 is a cross sectional view of a disinfection device 1000 according to embodiments of the present disclosure. As depicted, the disinfection device 1000 may be similar to the disinfection device 800, with the difference that a reflective coating 1003 may be formed on the outer surface of the container 1002. In embodiments, the reflective coating 1003 may be formed on the outer surface of the container 1002 except a region(s) where the disinfection light from the light source enters the container 1002 or a region(s) where the disinfection light exits the container toward the detector of the emitter-detector module 1050. In embodiments, the reflective coating 1003 may reflect the light toward the liquid, as indicated by an arrow 1040, to thereby prevent the disinfection light from escaping through the container 1002. In embodiments, the reflective coating 1002 may be formed of light reflecting material, such as aluminum, silver or distributed Bragg reflector (DBR), deposited on the outer surface of the container 1002.

Figure 11:
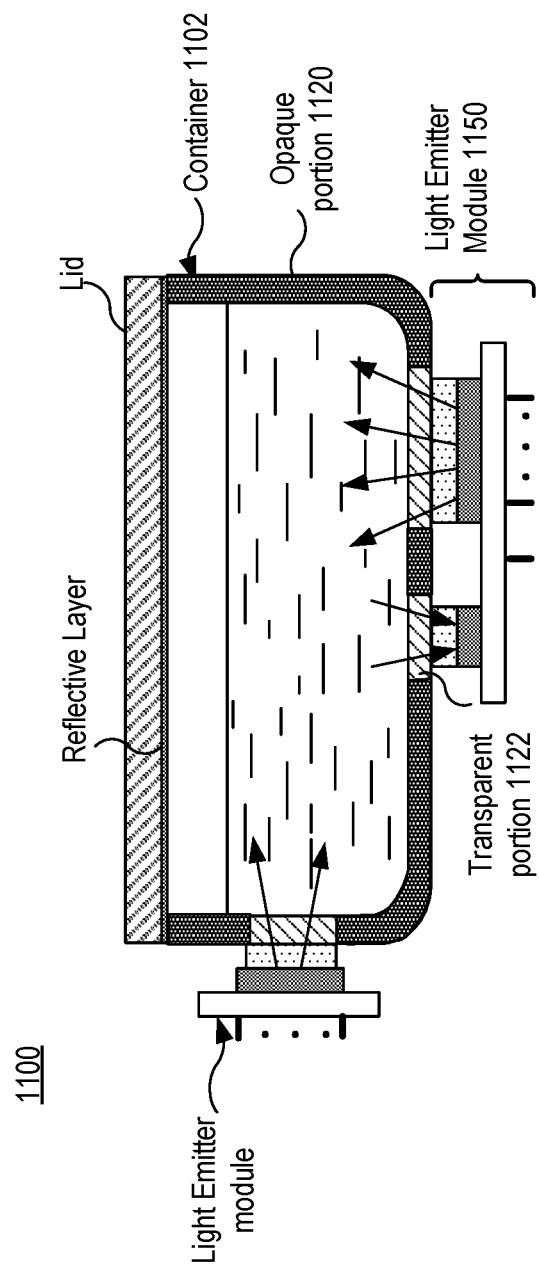
FIG. 11 is a cross sectional view of a disinfection device according to embodiments of the present disclosure.

FIG. 11 is a cross sectional view of a disinfection device 1100 according to embodiments of the present disclosure. As depicted, the disinfection device 1100 may be similar to the disinfection device 1000, with the difference that opaque portion 1120 may be used in place of the reflective coating 1003. In embodiments, the container 1102 may include the opaque portion 1120 and transparent portion 1122, where the disinfection light cannot pass through the opaque portion 1120. The transparent wall 1122 may be located at a region (s) where the disinfection light from the light source enters the container 1102 or a region(s) where the disinfection light exits the container toward the detector of the emitter-detector module 1150. In embodiments, the opaque portion 1120 may prevent the disinfection light from escaping the container 1102 through the container wall.

In FIGS. 5-11, each of the emitter-detector modules in FIGS. 5-11 is shown to have a detector and a light source. However, it should be apparent to those of ordinary skill in the art that each of the emitter-detector modules in FIGS. 5-11 may include other suitable number of detectors and light sources.

Figure 12:
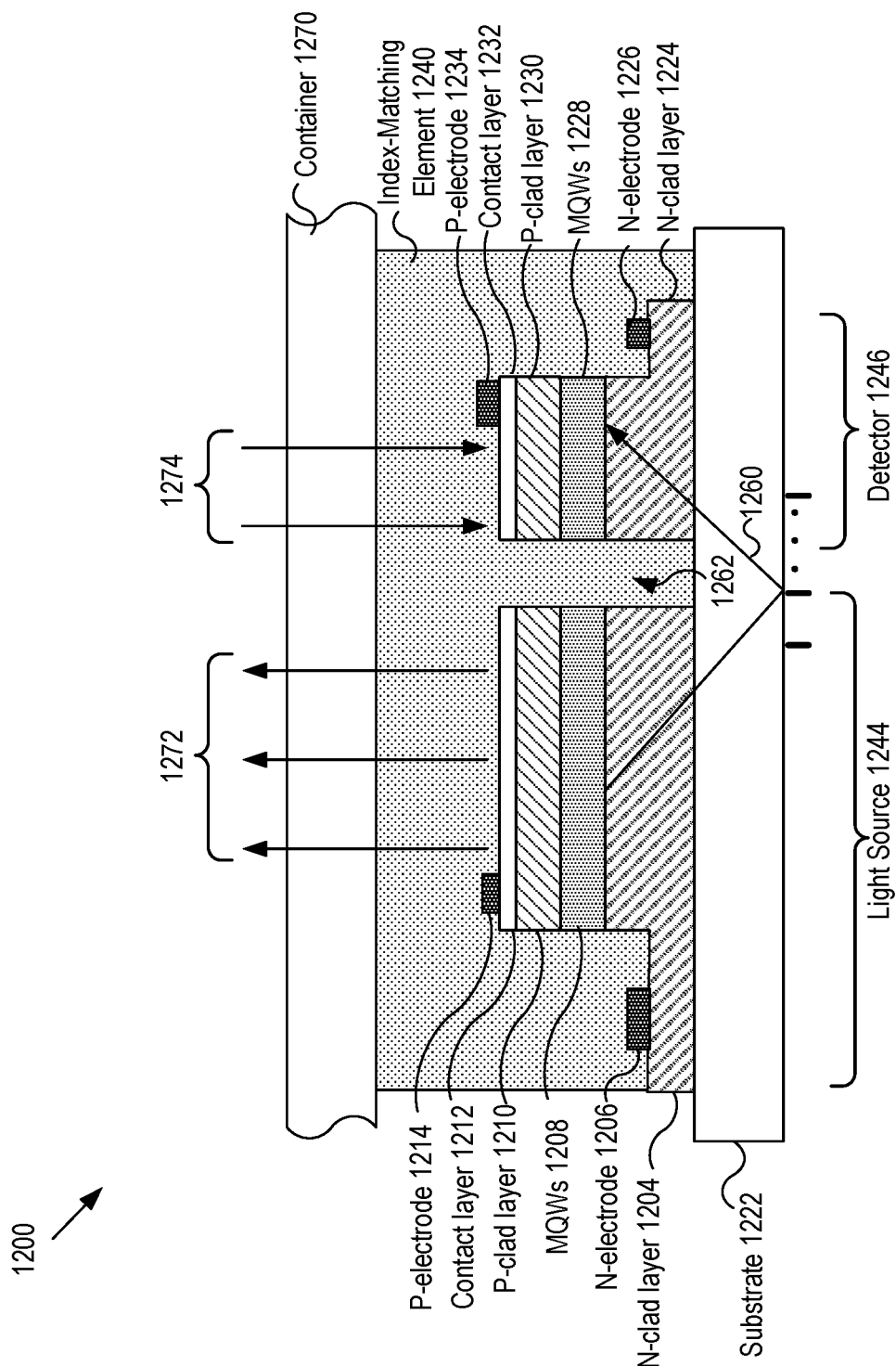
FIG. 12 is a cross sectional view of an emitter-detector module according to embodiments of the present disclosure.

FIG. 12 is a cross sectional view of an emitter-detector module 1200 according to embodiments of the present disclosure. As depicted, the emitter-detector module may include a light source 1244 and a detector 1246. In embodiments, the light source 1244 and detector 1246 may be similar to the light sources and detectors in FIGS. 5-11, respectively, with the difference that the light source 1244 and the detector 1246 are formed directly on the substrate 1222.

In embodiments, the light source 1244 may include: n-clad layer 1204, n-electrode 1206, multiple quantum well layers (MQWs) 1208, p-clad layer 1210, contact layer 1212, and p-electrode 1214. Similarly, in embodiments, the detector 1246 may include: n-clad layer 1224, n-electrode 1226, multiple quantum well layers (MQWs) 1228, p-clad layer 1230, contact layer 1232, and p-electrode 1234. In embodiments, the p-electrode 1214 and n-electrode 1206 may be anode and cathode, respectively, and the MQWs 1208 may generate disinfection light upon application of electrical potential across the p-electrode 1214 and n-electrode 1206. In embodiments, the p-electrode 1234 and n-electrode 1236 may be cathode and anode, respectively, and the MQWs 1228 may generate electrical current in response to the disinfection light.

In embodiments, the substrate 1222 may include electrical wires/traces (not shown in FIG. 12) for communicating electrical signals to the light source 1244 and the detector 1246. In embodiments, the substrate 1222 may be formed of material that is transparent to the disinfection light. In embodiments, a portion of the disinfection light generated by MQWs 1208 may be internally reflected at the bottom surface of the substrate 1222, as indicated by an arrow 1260. The current measured by the detector 1246 may be used to monitor the intensity of disinfection light generated by the light source 1244.

In embodiments, the light source 1244 and detector 1246 may be formed by suitable wafer processing techniques. In embodiments, since the light source 1244 and detector 1246 have the similar layer structure, each of the layers of the light source may be formed simultaneously with the corresponding layer of the detector. Then, a trench 1262 may be formed to separate the light source from the detector by a suitable process, such as etching, and an index-matching material is deposited over the light source and detector to form the index-matching element 1240. In embodiments, the trench 1262 may be also filled with the index-matching material.

In embodiments, the contact layer 1212 may be formed of electrically conducting material that is transparent to the disinfection light. The disinfection light generated by the light source 1244 may be transmitted to the container 1270 through the contact layer 1212 and index-matching element 1240, as indicate by arrows 1272. Also, similar to the devices in FIGS. 5-11, a portion of the disinfection light 1272 may be sent to the detector 1246 through the contact layer 1212 and index-matching element 1240, as indicated by arrows 1274. Since the detector 1246 may also receive the disinfection light that is internally reflected from the substrate 1222, as indicated by the arrow 1260, the detector 1246 may have two separate mechanisms to receive the disinfection light, which provides an enhanced stability in monitoring the intensity of light generated by the light source 1244.

Figure 13:
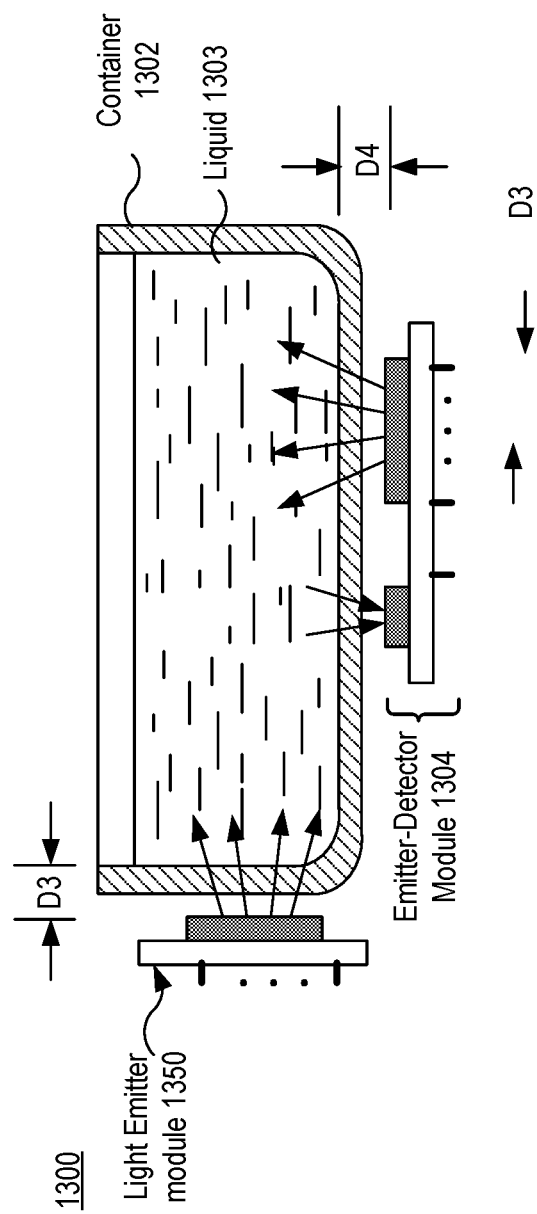
FIG. 13 is a cross sectional view of a disinfection device 1300 according to embodiments of the present disclosure.

In FIGS. 5-12, the index-matching element is in direct contact with both the container and light source. In alternative embodiments, the devices in FIG. 5-12 may be modified such that the index-matching elements are omitted. For instance, FIG. 13 shows a cross sectional view of a disinfection device 1300 according to embodiments of the present disclosure. As depicted, the disinfection device 1300 may be similar to the disinfection device 500, with the difference that the index-matching elements are omitted and the light-emitter module 1350 and the emitter-detector module 1304 are separated from the container 1302.

For each device in FIGS. 5-12, the index-matching element is in direct contact with both the container and light source. As such, the distance between the light source and the first light receiving surface of the liquid remains unchanged regardless of the volume of the liquid. Similarly, for each of the devices that are modified to omit the index-matching elements, the light source and container may be arranged so that the distance between the light source and the first light receiving surface of the liquid remains unchanged regardless of the volume of the liquid. For instance, the emitter-detector module 1304 may be in a spaced-apart relationship with the container 1302 so that the distance D3 between the light source of the emitter-detector module 1304 and the first light receiving surface of the liquid 1303 remains unchanged regardless of the volume of the liquid. Likewise, the light emitter module 1350 may be in a spaced-apart relationship with the container 1302 so that the distance D4 between the light source of the first light emitter module 1350 and the light receiving surface of the liquid 1303 remains unchanged regardless of the volume of the liquid.

Figure 14:
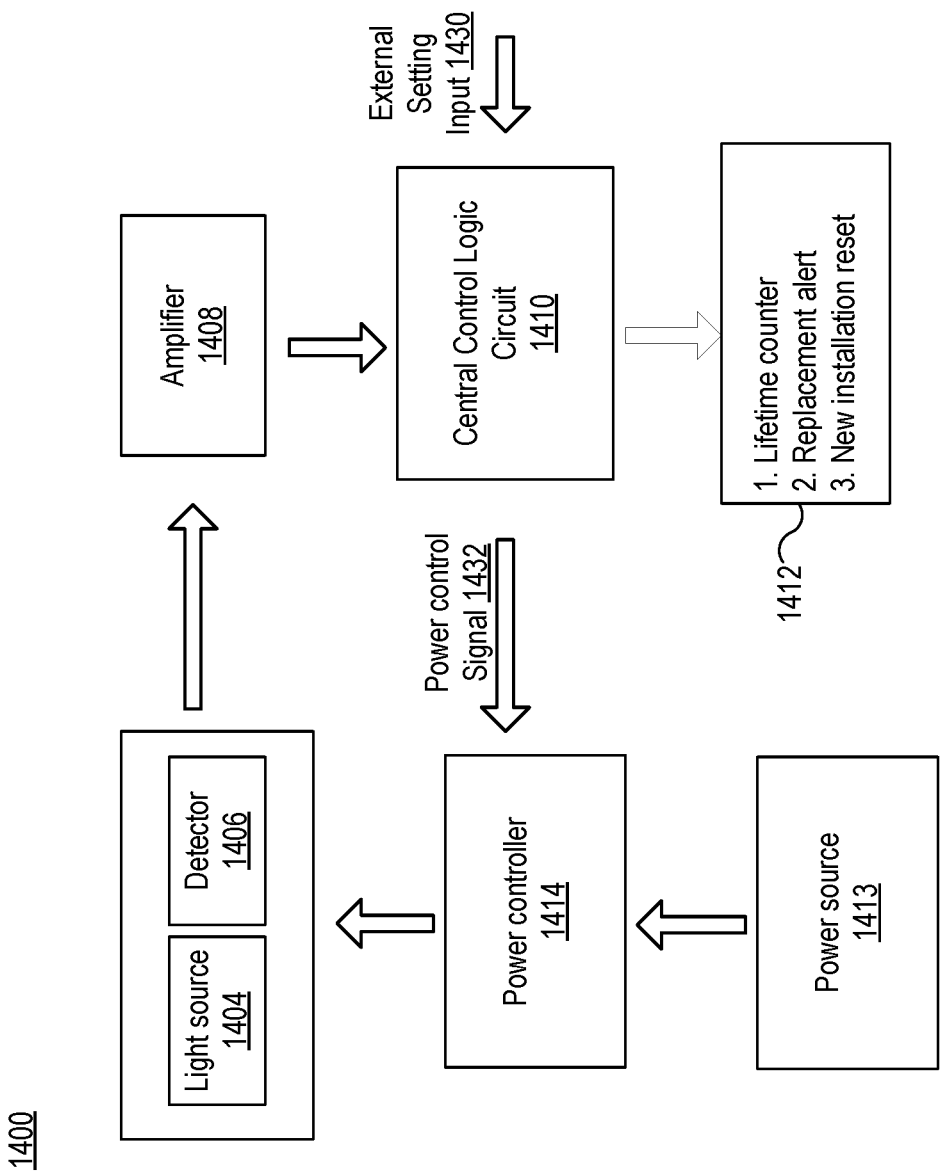
FIG. 14 shows an operational block diagram of a disinfection device according to embodiments of the present disclosure.

FIG. 14 shows an operational block diagram of a disinfection device 1400 according to embodiments of the present disclosure. As depicted, the light source 1404 (which may be similar to the light sources in FIGS. 5-13) generates disinfection light and a portion of the disinfection light is transmitted to the detector 1406 (which may be similar to the detectors in FIGS. 5-13) to monitor the intensity of the disinfection light generated by the light source 1404. In embodiments, the detector 1406 may be a photodiode and generate photocurrent in response to the light incident thereon. In embodiments, the photocurrent may be amplified by the amplifier 1408 and sent to the central control logic circuit (or shortly central controller) 1410.

A human operator may determine an operational intensity range of the output light generated by the light source 1404. Also, assuming that the responsivity of the detector 1406 and the gain of the amplifier 1408 do not vary in time, the human operator may determine the operational range of the photocurrent from the amplifier 1408 based on the operational intensity range of the output light generated by the light source 1404. In embodiments, the external setting input 1430, which may include the information of the operational range of the photocurrent, may be sent to the central controller 1410 via a suitable communication channel. It is noted that the external setting input 1430 may include other suitable information/control signal to program the central controller 1410.

In embodiments, the central controller 1410 may control the light source 1404 based on the operational range of the photocurrent. For instance, if the level of the photocurrent signal received from the amplifier 1408 is below the operational range, the central controller 1410 may send the power control signal 1432 to the power controller 1414 to increase the current (or power) input to the light source 1404. Likewise, if the level of the photocurrent signal received from the amplifier 1408 is above the operational range, the central controller 1410 may send the power control signal 1432 to the power controller 1414 to decrease the power input to the light source 1404. Thus, the amplifier 1408, central controller 1410, and power controller 1414 may form a feedback mechanism/loop for controlling the intensity of light emitted by the light source 1404. Hereinafter, the term feedback loop collectively refers to one or more components that participate in controlling the input current (or input power) to the light source 1404 based on the output signal from the detector 1406.

In embodiments, the power controller 1414 may receive electrical power from the power source 1413 through a wires and adjust the power (or current) input to the light source 1404 according to the power control signal 1432 received from the central controller 1410.

In embodiments, the central controller 1410 may send additional output signals to an external device(s) via a suitable communication channel, such as the wire, to thereby perform the extended functions 1412. For instance, the light source 1404 may be an UV light emitting diode (LED) and its output intensity may slowly decrease over time in a process, known as lumen depreciation. To monitor the operational lifetime of the light source 1404, the central controller 1410 may send control signals to a lifetime counter on a regular basis. In another example, the central controller 1410 may send a replacement alert when it determines that the intensity of the output light from the light source 1404 cannot be controlled by the feedback loop and the light source 1404 needs to be replaced. In yet another example, the central controller 1410 may send a reset signal when one of the components in the disinfection device 1400 is replaced and a new installation reset is needed. It is noted that the extended functions 1412 does not show an exhaust list of functions to be performed by the central controller 1410 for proper operation of the disinfection device 1400.

It is noted that one or more of the components in the disinfection device 1400 may be mounted on (or embedded in) a substrate (which is similar to the substrates in FIGS. 5-13). For instance, the central controller 1410 may be a chip that may be mounted on the substrate. In another example, the amplifier 1408 may be a circuit embedded in a PCB substrate.

It is also noted that one or more of the components in the disinfection device 1400 may be optional. For instance, the amplifier 1408 may be omitted if the photocurrent from the detector 1406 is high enough to be processed by the central controller 1410 without amplification. It is further noted that one or more of the components in the disinfection device 1400 may be combined into one component and/or one of the components in the disinfection device 1400 may be implemented as multiple components.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A disinfection device, comprising:
   a container having a wall that defines a chamber for containing liquid therein;
   a light source for transmitting disinfection light to the liquid and disposed outside of the container, wherein the disinfection light transmitted by the light source passes through the wall of the container and subsequently enters the chamber; and
   a detector for generating an electrical signal responsive to receiving a portion of the disinfection light and disposed outside of the container, wherein the portion of the disinfection light travels from inside of the chamber to the outside of the container and passes through the wall of the container to reach the detector,
   wherein the light source is in a spatial relationship with the container so that a distance between the light source and a first light receiving surface of the liquid remains unchanged regardless of a volume of the liquid,
   wherein a first layer formed of a material that is transparent to the disinfection light is disposed on a top surface of the light source and a second layer formed of the material is disposed on a top surface of the detector and wherein both the first and second layers are in direct contact with the wall of the container.

2. The disinfection device of claim 1, wherein the light source and the detector are mounted on a substrate that is disposed outside of the container.

3. The disinfection device of claim 2, wherein a portion of disinfection light generated by the light source is internally reflected by the substrate and transmitted to the detector.

4. The disinfection device of claim 1, further comprising:
   a lid for covering the chamber and including a reflective layer that is formed on a surface of the lid and reflects the disinfection light.

5. The disinfection device of claim 1, further comprising:
   a diffusing element disposed on an inner surface of the wall of the container and configured to diffuse the disinfection light.

6. The disinfection device of claim 5, wherein the diffusing element is a diffuser attached to a surface of the wall of the container.

7. The disinfection device of claim 1, further comprising:
   a reflective coating formed on an outer surface of the wall of the container and configured to reflect the disinfection light.

8. The disinfection device of claim 1, wherein the container wall includes a transparent portion that is formed of material transparent to the disinfection light and an opaque portion that is formed of material opaque to the disinfection light.

9. The disinfection device of claim 1, wherein the first and second layers are formed of one monolithic layer and a portion of the disinfection light transmitted by the light source is internally reflected within the monolithic layer so as to reach the detector without entering the container.

* * * * *